United States Patent [19]

May et al.

[11] Patent Number: 4,462,813
[45] Date of Patent: Jul. 31, 1984

[54] SYSTEM AND METHOD FOR CONVERTING WELLHEAD GAS TO LIQUEFIED PETROLEUM GASES (LPG)

[75] Inventors: Ronald L. May, Kingwood; Bobby W. Sinclair, Wichita Falls, both of Tex.

[73] Assignee: Sappsucker, Inc., Houston, Tex.

[21] Appl. No.: 557,852

[22] Filed: Dec. 5, 1983

Related U.S. Application Data

[63] Continuation-in-part of Ser. No. 369,159, Apr. 19, 1982, Pat. No. 4,419,114.

[51] Int. Cl.$^3$ .............................. F25J 3/00; F25J 5/00
[52] U.S. Cl. .......................................... 62/17; 62/20; 62/21; 62/29; 62/37; 62/40
[58] Field of Search .................... 62/17, 20, 9, 11, 19, 62/21, 23, 26, 30, 40, 41, 29, 37; 55/27, 29, 30, 40-43, 68

[56] References Cited

U.S. PATENT DOCUMENTS

| | | | |
|---|---|---|---|
| 2,198,098 | 4/1940 | Vaughan | 62/23 |
| 2,217,749 | 10/1940 | Hewitt | 62/23 |
| 2,814,936 | 12/1957 | Morrison | 62/9 |
| 2,896,414 | 7/1959 | Tung | 62/11 |
| 2,900,796 | 8/1959 | Morrison | 62/11 |
| 3,791,157 | 2/1974 | Tracy et al. | 62/41 |

*Primary Examiner*—Frank Sever
*Attorney, Agent, or Firm*—Bill B. Berryhill

[57] ABSTRACT

A method of converting natural wellhead gas to liquefied petroleum gases (LPG) may comprise the steps of: separating natural gas from petroleum fluids exiting a wellhead; compressing the natural gas; refrigerating the natural gas, liquefying at least a portion thereof; separating LPG from gas vapors of the refrigerated natural gas; storing the separated LPG in a storage tank with a vapor space therein; and recirculating a portion of the LPG vapors in the storage tank with the natural gas exiting the wellhead to enhance recovery of LPG. A system for performing the method may comprise: a two-stage gas compressor connected to the wellhead; a refrigeration unit downstream of the gas compressor for refrigerating the compressed gases therefrom; at least one product separator downstream of the refrigerator unit for receiving refrigerated and compressed gases discharged from the refrigerator unit and separating LPG therein from gases remaining in vapor form; and a storage tank for receiving and storing the separated LPG therein, the storage tank having a vapor space therein connected upstream of the gas compressor through a pressure regulator allowing recirculation of some LPG vapors with the natural gases through said system.

22 Claims, 1 Drawing Figure

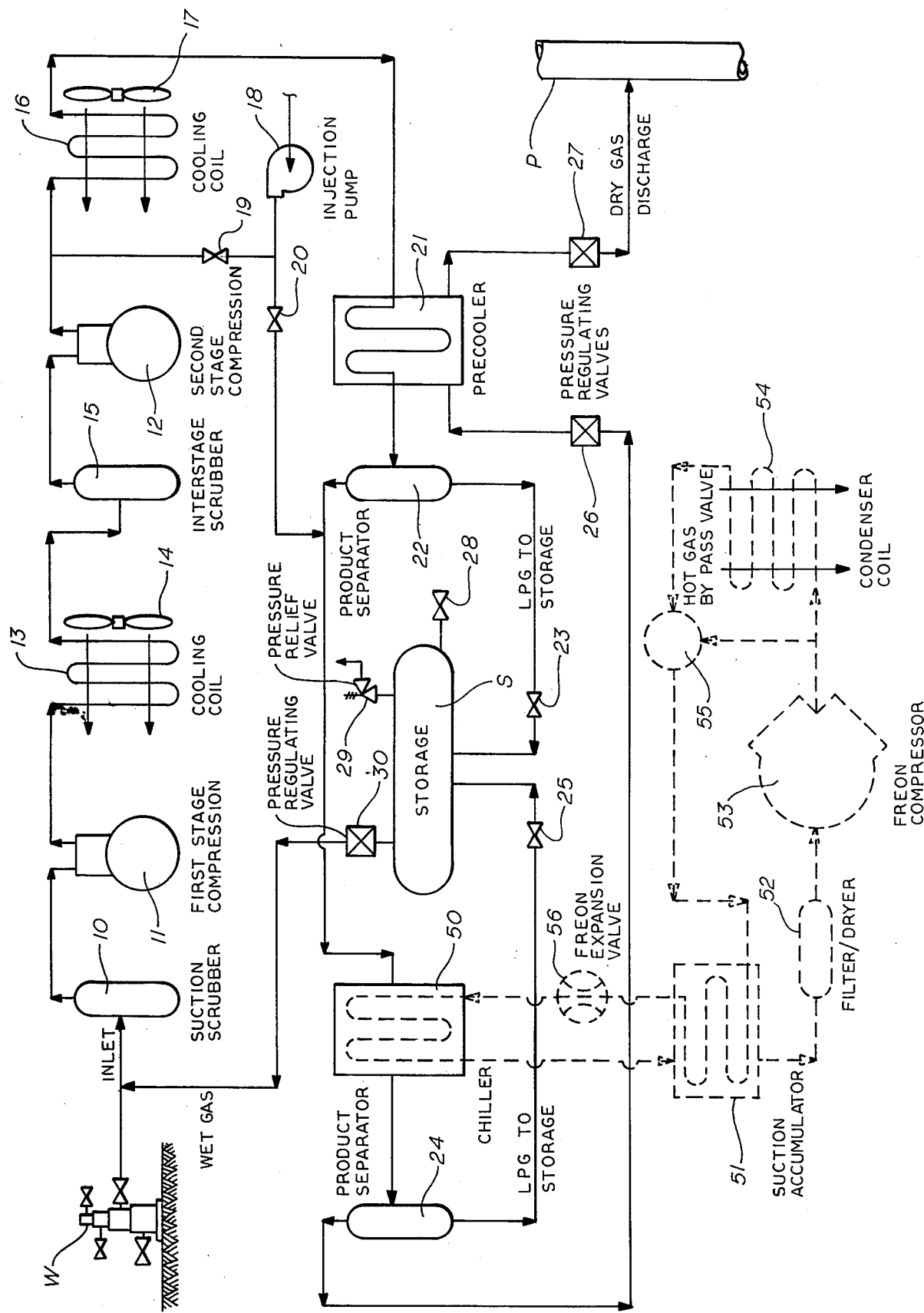

SYSTEM AND METHOD FOR CONVERTING WELLHEAD GAS TO LIQUEFIED PETROLEUM GASES (LPG)

CROSS-REFERENCE TO RELATED APPLICATION

The present application continuation-in-part of patent application Ser. No. 369,159, filed Apr. 19, 1982, issued as Pat. No. 4,419,114 on Dec. 6, 1983.

BACKGROUND OF THE INVENTION

1. Field of the Invention

The present invention pertains to methods and systems for the production of liquefied petroleum gases (LPG). Specifically, it pertains to systems and methods for converting natural wellhead gas to LPG.

2. Brief Description of the Prior Art

Gas wells of sufficient volume are normally connected to a gas pipeline for transporting the natural gas to natural gas markets. While the gas may be separated from hydrocarbon liquids exiting the well and dried, it is basically left in its natural form for such transportation to market.

Some natural gases may be converted to liquefied petroleum gas (LPG). The primary advantage of LPG is its ability to be transported by truck or rail to ultimate points of use not capable of supporting a pipeline. For example, LPG is widely used on farms for heating, crop drying and dehydration, tobacco drying, flame cultivation, irrigation pumps, cotton ginning, and stationary engine operations. In addition, many farmers use LPG to operate their tractors. Many buses, trucks, fork-lifts and the like use LPG.

Large industrial and manufacturing companies have found LPG to be an answer to heating problems because of its high purity, constant quality and competitive cost as compared with other types of gases and liquid fuel. Many small city gas plants utilize LPG. Refineries may use LPG in the manufacture of various grades of gasoline and high-octane motor fuels. LPG is used as basic raw material in the manufacture of many plastic synthetic fibers, synthetic rubber, etc.

In recent years, gas wells which were isolated or otherwise not easily connected to a gas pipeline have been provided with processing units for converting some of the natural gas to LPG. Thus, the LPG produced thereby can be stored in a tank for transportation by truck or railcar. However, such processing units usually require gas production in excess of 1000 MCFD. This eliminates many wells which produce less than 1000 MCFD. Thus, such wells must be either shut in or, if produced for their liquid hydrocarbon content, must be flared, wasting the gas produced thereby.

In U.S. Pat. No. 4,419,114, which issued from the parent of the present application, a system and method are disclosed for converting natural wellhead gas to LPG. The term "natural wellhead gas" as used herein refers also to "casing head" or "residue" gas. The method and system of U.S. Pat. No. 4,419,114 are specifically designed for wells producing less than 1000 MCFD. Thus, previously uneconomical wells may be produced so as to contribute to solving the current energy shortage while producing significant income to the well owner and the gas processor.

The system of U.S. Pat. No. 4,419,114 comprises a gas compressor connected to the wellhead for compressing natural gases received therefrom, refrigeration means downstream of the gas compressor for cooling the compressed gases therefrom and produce separator means downstream of the refrigeration means for receiving cooled and compressed gases discharged from the refrigeration means and separating LPG therein from gases remaining in vapor form. A storage tank may be provided for receiving LPG exiting from the product separator means for storing the LPG under pressure therein. The system of U.S. Pat. No. 4,419,114 is especially characterized by providing means for unloading the gas compressor in the event of its suction pressure falling below a predetermined level. Thus, the system is continuously operable even when incoming pressures fall below a safe level, e.g. 2 psig. The gas compressor simply cycles or idles under such conditions, preventing build-up of temperatures or entry of air into the system which might well occur without such an unloading means and if such did occur could cause hazardous explosions. While the system of U.S. Pat. No. 4,419,114 has proven to be economical and practical, the means for unloading the gas compressor is not without problems.

SUMMARY OF THE INVENTION

Like the system disclosed in U.S. Pat. No. 4,419,114, the system and method of the present invention are for partially converting natural wellhead gas to LPG and is specifically designed for wells producing less than 1000 MCFD. The system of the present invention includes two-stage gas compressor means connected to the wellhead for compressing natural gases received therefrom, refrigeration means in heat exchange with the compressed natural gases downstream of the gas compressor means for refrigerating the compressed gases; product separator means for receiving cooled and compressed gases and separating LPG therein from gases remaining in vapor form, and storage means connected to the product separator means for receiving and storing the separated LPG therein. The storage means has a vapor space which is connected to the suction side of the gas compressor means by a conduit having a pressure regulator therein. The pressure regulator maintains pressure in the vapor space but allows flow of hydrocarbon vapors from the vapor space when the vapor pressure therein exceeds a predetermined value. Thus, certain hydrocarbon vapors are recirculated with natural gases from the wellhead through the system.

The product separator means is also divided into stages so that some product separation takes place prior to refrigeration of the gas stream. Thus, some water and LPG are removed before refrigeration decreasing the amount of methanol required. Furthermore, the gases separated from LPG are drier resulting in less problems in pipeline transportation of the gas. In addition, refrigeration costs are reduced by eliminating the cooling of water and heavier LPG in the system.

Like in the system of U.S. Pat. No. 4,419,114, the system and method of the present invention are relatively simple and compact. The system can be manufactured on a unitized skid suitable for transportation by truck or rail for easy installation at the wellhead. Power for the entire system may be supplied by a natural gas engine driven by gas supplied from the system itself. Thus, natural gas which has been previously uneconomical for production is recovered or can be recovered and converted to LPG for easy storage and transportation. Specifically, wells producing natural gas below 1000 MCFD, not previously producible, can be made to contribute to solving our energy shortage and to the economic wellbeing of the well owners and processors. The system and method of the present invention is extremely efficient in production and energy costs. Many other objects and advantages of the invention can be seen from reading the specificaion which follows in conjunction with the accompanying drawing.

DESCRIPTION OF THE DRAWING

The drawing is a schematic flow diagram illustrating the system and method for converting the natural wellhead gas to LPG according to a preferred embodiment of the invention.

DESCRIPTION OF A PREFERRED EMBODIMENT

Referring to the schematic flow diagram of the drawing, the system and method of converting natural wellhead gas to LPG containing ethane ($C_2$), propane ($C_3$), butane ($C_4$) and petroleum gases of lesser vapor pressures ($C_{5+}$) will be described. Natural wellhead or wet gas from a wellhead W is introduced at the inlet of the system of the present invention for processing therethrough and for eventual discharge of dry gas [primarily methane ($C_1$) and ethane ($C_2$)] into a pipeline P and storage of LPG in a storage tank S. The LPG may be transferred from the storage tank S by truck or rail and the dry gas at the discharge may be transferred by the pipeline P into a gathering system or some other means for distributing gas.

The natural wellhead gas entering the system may contain both natural gas and petroleum liquids. In fact, most all gas wells produce some amount of hydrocarbon liquids. The term "natural wellhead gas" as used in the specification and claims refers to any such gas whether it is called "wellhead gas", "casing head gas", "residue gas" or the like. The natural wellhead gas entering the system of the present invention first passes through a suction scrubber 10 where any petroleum liquids are separated from natural gases and collected in the lower portion thereof. Upon liquids reaching a predetermined level in the scrubber 10, liquid level control devices (not shown) allow the liquids to be dumped to discharge as waste or collected for other use. The suction scrubber 10 may be provided with the usual safety and operational devices (not shown).

From the suction scrubber 10, the natural gases flow through two-stage gas compressor means comprising first-stage compression 11 and second-stage compression 12. In the first-stage compression 11, the natural gas is compressed at a compression ratio of approximately 4:1. Thus, the gas entering the first-stage compression 11, e.g. at 10 psig (assuming atmospheric pressure of 14.5 psi) exits at a pressure of approximately 83.5 psig. The first-stage compression 11 and second stage compression 12 may, of course, be separate compressors or simply two stages of a single compressor driven by a single power source (not shown).

As the gas is compressed in the first-stage compressor 11 its temperature increases, e.g. 125°–140° F. To reduce the temperature of the compressed gas, it passes through a cooling coil 13 across which air is blown by a blower 14. Cooled gases leaving the cooling coil 13 pass through an interstage scrubber 15 where any liquids therein are separated from the gases. The liquids separated at this point are generally natural gasolines. The natural gasolines are collected in the interstage scrubber 15 and upon reaching certain levels are discharged to a collection point. Normal liquid level, pressure control and safety devices (not shown) are provided.

From the interstage scrubber 15, the partially compressed gases are routed to the second stage compression 12 for further compression. Here the gases may again be compressed at a compression ratio of approximately 4:1, exiting from the second stage compression 12 at maximum pressures of approximately 300 psig or a range of 225 psig to 300 psig. The temperature of the gases is of course increased and therefore the gas is passed through another cooling coil 16 for cooling by air from a blower 17. Of course, the cooling coils 13 and 16 can be situated together and cooled by a single blower if desired. To prevent water in the system from freezing during cooling, particularly in the winter, an injection pump 18 may be provided to inject methanol or some other antifreeze solution through valve 19 into the gas stream. It will be noted that the injection pump is also connected by a valve 20 to a further downstream position in the system primarily for summer conditions.

The compressed and partially cooled gases exiting from the cooling coil 16 are then routed through the tube side of a shell and tube precooler 21. The shell side of the precooler 21 contains gases at lower temperatures just prior to discharge of these gases from the system into the pipeline P. Thus, heat exchange takes place, raising the temperature of the gases in the shell side and further lowering the temperature of the compressed gases in the tube side of the precooler 21. The partially cooled gases can also be in the shell and the colder gases in the tubes so that the precooler can also be used as a product separator to decrease manufacturing costs. In either event, cooling of the compressed gases takes place in the cooling coils 13 and 16 and the precooler 21.

From the precooler 21, the compressed and cooled gases enter a first product separator 22. By the time the gases reach the first product separator 22 they have been compressed and cooled sufficiently so that some of the heavier hydrocarbons therein exist in liquid form (LPG). The LPG collected in the product separator 20 can then be transferred through a discharge valve 23 to a storage tank S. At this point, any water existing in the system is also separated and transferred. Therefore, no further cooling of water and heavier LPG is required downstream thereof. This results in a substantial reduction in cooling costs and in the cost of methanol or other antifreeze solutions. As the remaining gases exit from the first product separator 22 they may be injected with methanol (particularly under summer conditions) through the valve 20.

From the product separator 22 the compressed and partially cooled gases are passed through the shell side of a chiller 50 which is a component of a refrigeration means or system utilized with the invention which also includes a suction accumulator 51, filter/dryer 52, freon compressor 53, condensor coil 54, hot gas bypass valve 55, and freon expansion valve 56. The refrigeration system is a typical one in which refrigerant in vapor form passes from the suction accumulator 51 through the filter/dryer 52 to the compressor 53 for compression into liquid form. The liquid refrigerant normally passes through the condenser coil 54 for cooling. In certain cases for temperature and efficient control, the freon may bypass the condenser 54 via the bypass valve 55. The liquid refrigerant passes through the coil side of the suction accumulator 51 for heat exchange with the vaporized refrigerant therein. Refrigerant is then passed through the expansion valve 56 and exits as a very low pressure liquid which boils off and absorbs heat from the processed gas in the shell of chiller 50, lowering the gas temperature to tie processed temperature. The then gaseous freon is returned to the freon compressor 53 through the suction accumulator 51 and filter/dryer 52 to repeat the cycle.

From the chiller 50, the gases flow to a second product separator 24. By the time the gases reach the second product separator 24, they have been cooled to the range of approximately 0° F. to −20° F. and are at a pressure of approximately 250 psig to 300 psig. Under these conditions, ethanes, propanes, butanes, etc. exist in liquid form (LPG). The LPG collected in the product separator 24 can then be transferred to the discharge valve 25 to storage tank S. Various liquid level and pressure control devices (not shown) may be provided at the product separator 24.

The cold gases remaining in vapor form in the product separator 24 are then routed via a pressure regulating valve 26 through the shell side of the precooler 21. Heat exchange therefore takese place in the precooler 21 between the cold gases and the cool but relatively warmer gases in the tube side of the precooler 21. The hot and cold gases can be interchanged in the tube shell to facilitate making the precooler 21 a product separator. The essentially dry gas (methane and ethane) are then discharged into the pipeline P through a regulator valve 27. The regulator valve 27 maintains a system pressure of approximately 250 psig to 300 psig. The dry gas being discharged into the pipeline P has most of the LPG removed therefrom and is primarily methane and ethane.

The gases being discharged from the system are dry and at a pressure of approximately 250 psig. This gas is useful in supplying the pressure and gas needed for operation of various other components of the system. For example, a natural gas engine (not shown) may be provided for supplying power to compressor means 11, 12, cooling means blowers 14, 17, freon compressor 53, etc. Pressure regulators (not shown) may be provided for supplying such gas at the required pressures.

The storage tank S may be provided with one or more valves 28 for removal of LPG therefrom. In such storage tanks, the LPG normally exists in a liquid phase and in the upper portion thereof a vapor phase. The tank may be provided with a relief valve 29 connected to the vapor space for relieving excessive pressures therein. Another and extremely important aspect of the system of the present invention is the connection of the vapor space back to the inlet of the system through a pressure regulating valve 30. The pressure regulating valve 30 maintains a predetermined vapor pressure in the storage tank S but when vapor pressure exceeds predetermined amounts, e.g. 215 psig for 100° F. days and 140 psig for 60° F. days, the valve opens permitting some of the vapors to return to the inlet of the system for recirculation with natural gas from the wellhead W. It has been found that enriching the inlet gas stream by this method substantially enhances the recovery of LPG (ethane, propane, butanes, etc.). For example, recovery of propane may be increased by as much as twenty-one percent (21%), or the total mix of $C_2$ through $C_{6+}$ by as much as sixteen percent (16%).

Thus, the system and method of the present invention provide a unique method of economically converting natural gas from a well, preferably producing at a rate of 1000 MCFD to LPG. LPG recovery is substantially enhanced by recirculation of vapors from the storage tank through the system. By providing at least two-stage product separation, one stage after cooling but prior to refrigeration. This is extremely cost effective, reducing methanol cost and reducing cooling capacity which otherwise would be necessary for cooling of water and heavier LPG in the system. Not only does the present system result in greater recovery of LPG, the remaining gas is well dehydrated preventing problems in pipeline transportation associated with too much water.

While a single embodiment of the invention has been described herein, many variations thereof may be made without departing from the spirit of the invention. Accordingly, it is intended that the scope of the invention be limited only by the claims which follow.

We claim:

1. A system for converting natural wellhead gas to liquefied petroleum gases (LPG) containing propane and petroleum gases of lesser vapor pressures comprising components sized and designed to process wells producing less than 1000 MCFD, including:
   gas compressor means connected to said wellhead for compressing natural gases received therefrom;
   refrigeration means in heat exchange with said compressed natural gases downstream of said gas compressor means for refrigerating the compressed gases therefrom;
   product separator means for receiving refrigerated and compressed gases and separating LPG therein from gases remaining in vapor form; and
   storage means connected to said product separator means for receiving and storing said separated LPG therein, said storage means having a vapor space therein connected upstream of said gas compressor means by a conduit having pressure regulation means therein for maintaining pressure in said vapor space but allowing flow of LPG vapors from said vapor space when the vapor pressure therein exceeds a predetermined value, thereby recirculating some of said LPG vapors with said natural gases from said wellhead through said compressor means, said refrigeration means and said product separator means.

2. A system for converting natural wellhead gas to liquefied petroleum gases (LPG) as set forth in claim 1 in which said compressor means includes first and second compression stages and including first scrubber means upstream of said gas compressor means and second scrubber means between said first and second stages of said gas compressor means for removing liquid from said wellhead gas which might be harmful to said gas compressor means.

3. A system for converting natural wellhead gas to liquefied petroleum gases (LPG) as set forth in claim 1 including cooling means through which gases compressed by said gas compressor means passes prior to passage through said refrigeration means.

4. A system for converting natural wellhead gas to liquefied petroleum gases (LPG) as set forth in claim 3 in which said cooling means includes cooling coils and an air blower providing ambient air for cooling of said compressed gases passing through said cooling coils.

5. A system for converting natural wellhead gas to liquefied petroleum gases (LPG) as set forth in claim 3 in which said cooling means includes a precooler through which said gases remaining in vapor form discharged from said product separator means pass for heat exchange with said compressed gases for cooling said compressed gases prior to passage through said product separator means.

6. A system for converting natural wellhead gas to liquefied petroleum gases (LPG) as set forth in claim 3 in which said product separator means comprises a first product separator downstream of said cooling means and upstream of said refrigeration means and a second product separator downstream of said refrigeration means.

7. A system for converting natural wellhead gas to liquefied petroleum gases (LPG) as set forth in claim 1 in which said refrigeration means includes a chiller through which compressed gases from said gas compressor pass for heat exchange with refrigerant therein.

8. A system for converting natural wellhead gas to liquefied petroleum gases (LPG) as set forth in claim 7 including injection means connected downstream of said compressor means and upstream of said refrigeration means for injecting antifreeze fluids to prevent freezing of water in said system.

9. A system for converting natural wellhead gas to liquefied petroleum gases (LPG) as set forth in claim 7 in which said product separator means includes a first product separator upstream of said chiller and a second product separator downstream of said chiller.

10. A system for converting natural wellhead gas to liquefied petroleum gases (LPG) as set forth in claim 9 in which said injection means is connected downstream of said first product separator and upstream of said chiller.

11. A system for converting natural wellhead gas to liquefied petroleum gases (LPG) as set forth in claim 1 in which said pressure regulator means is set to allow said flow of LPG vapors from said vapor space at a predetermined pressure in a range of 140 psig to 215 psig.

12. A method of converting natural wellhead gas to liquefied petroleum gases (LPG) containing propane and petroleum gases of lesser vapor pressures comprising the steps of:
separating natural gas from petroleum fluids exiting a wellhead producing less than 1000 MCFD;
compressing said natural gas;
cooling said compressed natural gas;
refrigerating said compressed natural gas to liquefy at least a portion thereof;
separating LPG from gas vapors of said refrigerated compressed natural gas;
storing said separated LPG in a storage tank having a vapor space therein;
recirculating a portion of the LPG vapors in said vapor space with said natural gas exiting said wellhead to enhance the recovery of LPG.

13. A method of converting natural wellhead gas to LPG as set forth in claim 12 in which said cooling of said compressed natural gas is at least partially performed by passing said compressed natural gas through a precooler for heat exchange with gas vapors of said refrigerated compressed natural gas.

14. A method of converting natural wellhead gas to LPG as set forth in claim 12 in which some LPG and water are separated from gas vapors of said cooled and compressed natural gas prior to said refrigerating said compressed natural gas, removing said water prior to said refrigerating said compressed natural gas.

15. A method of converting natural wellhead gas to LPG as set forth in claim 14 including the additional step of injecting antifreeze fluids into said compressed natural gas prior to said refrigerating thereof.

16. A method of converting natural wellhead gas to LPG as set forth in claim 12 in which said natural gas is compressed to a pressure of approximately 225 psig to 300 psig and in which said recirculation of a portion of the LPG vapors in said vapor space is allowed when the vapor pressure in said vapor space reaches a predetermined value in a range of 140 psig to 215 psig.

17. A method of converting natural wellhead gas to liquefied petroleum gases (LPG) containing propane and petroleum gases of lesser vapor pressures comprising the steps of:
separating natural gas from petroleum fluids exiting a wellhead producing less than 1000 MCFD;
compressing said natural gas in the first stage of a two-stage gas compressor;
cooling said compressed natural gas;
further compressing said natural gas in the second stage of said two-stage gas compressor;
cooling said further compressed natural gas;
separating LPG from gas vapors of said cooled and compressed natural gas and storing said separated LPG in a storage tank having a vapor space therein;
refrigerating said gas vapors separated from said cooled and compressed natural gas further liquefying at least a portion thereof;
separating LPG from said refrigerated gas vapors and storing said LPG in said storage tank; and
recirculating a portion of the LPG vapors in said vapor space with said natural gas exiting said wellhead to enhance the recovery of LPG.

18. A method of converting natural wellhead gas to LPG as set forth in claim 17 in which said cooling of said further compressed natural gas is at least partially accomplished by passing said compressed natural gas through a precooler for heat exchange with said refrigerated gas vapors after said LPG separation therefrom.

19. A method of converting natural wellhead gas to LPG as set forth in claim 17 in which most water existing in said cooled and compressed natural gas is separated with said LPG prior to said refrigerating step.

20. A method of converting natural wellhead gas to LPG as set forth in claim 19 including the step of injecting antifreeze solutions into said cooled and compressed natural gas after said separation of LPG and water therefrom but prior to said refrigeration step.

21. A method of converting natural gas to LPG as set forth in claim 17 in which said recirculation of a portion of LPG vapors in said vapor space is accomplished through a conduit in communication with said vapor space through a regulator valve, said regulator valve being set to permit flow of vapors from said vapor space when the vapor pressure therein is above a predetermined pressure.

22. A method of converting LPG to natural gas as set forth in claim 21 in which said predetermined pressure is in a range of approximately 140 psig to 215 psig.

* * * * *